United States Patent [19]

Spielau et al.

[11] Patent Number: 4,666,956
[45] Date of Patent: May 19, 1987

[54] BIOCIDAL COMPOSITION AND ITS USE IN PLASTIC MOLDING COMPOUNDS

[75] Inventors: Paul Spielau; Horst Vohwinkel, both of Troisdorf-Eschmar; Peter Pütz, Augustin 3/Menden, all of Fed. Rep. of Germany

[73] Assignee: Dynamit Nobel Ag, Colonge, Fed. Rep. of Germany

[21] Appl. No.: 767,690

[22] Filed: Aug. 20, 1985

Related U.S. Application Data

[63] Continuation of Ser. No. 659,495, Oct. 9, 1984, abandoned, which is a continuation of Ser. No. 532,818, Sep. 16, 1983, abandoned, which is a continuation of Ser. No. 307,143, Sep. 30, 1981, abandoned.

[30] Foreign Application Priority Data

Oct. 1, 1980 [DE] Fed. Rep. of Germany ....... 3037022

[51] Int. Cl.$^4$ .............................................. C08K 5/59
[52] U.S. Cl. .................................... 523/122; 524/177
[58] Field of Search .......................... 106/18.34, 15.05; 523/122; 524/177, 108, 180, 399, 405, 417, 423, 434; 514/504

[56] References Cited

U.S. PATENT DOCUMENTS

| | | | |
|---|---|---|---|
| 3,069,252 | 12/1962 | Josephs et al. | 514/504 |
| 3,214,281 | 10/1965 | Nagasawa | 106/15.05 |
| 3,288,674 | 11/1966 | Yeager | 514/504 |
| 3,288,830 | 1/1966 | McFadden et al. | 514/504 |
| 3,558,783 | 1/1971 | Leebrick et al. | 524/177 |
| 3,689,449 | 9/1972 | Yeager et al. | 106/18.34 |
| 3,801,534 | 4/1974 | Beers | 523/122 |
| 3,896,753 | 7/1975 | Shepherd et al. | 523/122 |
| 4,049,822 | 9/1977 | Rei et al. | 514/504 |
| 4,086,297 | 4/1978 | Rei et al. | 523/122 |
| 4,166,111 | 8/1979 | Carderelli | 514/493 |
| 4,191,580 | 3/1980 | Beiter et al. | 523/122 |

FOREIGN PATENT DOCUMENTS

| | | |
|---|---|---|
| 2013792 | 10/1970 | Fed. Rep. of Germany . |
| 1122371 | 8/1968 | United Kingdom . |
| 1169288 | 11/1969 | United Kingdom . |

OTHER PUBLICATIONS

Eisenschiml, R., "Microbial Degradation of . . . Vinyl Films", Stabilization of Polymers and Stabilizer Processes—Advances in Chemistry Series 85, Am. Chem. Socty, (1968), pp. 250-271.
Tirpak, George, "Microbial Degradation of Plasticized PVC"—SPE Journal, Jul. 1970, vol. 26, pp. 26 to 30.
Ketchum et al., "Action of Antifouling Paints", Ind. Eng. Chem., vol. 38, No. 9, pp. 931-936, Sep. 1966.
Dunn et al., "A Novel Conceptin Marine Antifouling Elastomers", Rubber Industry, Feb. 1975, pp. 34 to 41.
A. K. Sawyer, "Organotin Compounds", Band 3, 1972, Seiten 933-940, N.Y.
K. Thinius, "Stabilisierung und Alterung von Plastwerkstoffen", Band 1, 1969, Seiten 157-159.

*Primary Examiner*—Veronica P. Hoke
*Attorney, Agent, or Firm*—Felfe & Lynch

[57] ABSTRACT

A biocidal composition based on organic arsenic compounds, comprising at least one tin compound in an amount affective to prevent elution of the arsenic compound from a composition containing them, particularly molding compositions for the production of molded plastic articles, particularly based on flexible PVC and/or ethylene/vinyl acetate copolymers or graft polymers or, optionally, polyethylene, containing stabilizers imparting stability to light, weather and heat, and optionally conventional additives such as colorants, fillers and slip agents, and containing further an arsenic compound as a biocidal agent are treated with such tin compound to prevent elution of the biocidal compound.

15 Claims, No Drawings

BIOCIDAL COMPOSITION AND ITS USE IN PLASTIC MOLDING COMPOUNDS

This application is a continuation of application Ser. no. 659,495, filed Oct. 10, 1984, which is a continuation of application Ser. No. 532,818, filed Sept. 16, 1983, which is a continuation of application Ser. No. 307,143, filed Sept. 30, 1981, all now abandoned.

The invention relates to a biocidal composition based on organic arsenic compounds and to the use of said composition in plastic molding compounds.

For the purposes of this invention, biocidal agents are substances designed to protect plastics against biological attack. The latter may be attributable to a variety of organisms, such as algae, fungi, bacteria, marine parasites, vermin, etc.

The requirements which biocidal agents must meet may be defined as follows:

A broad spectrum of antimicrobial activity.
Effectiveness in low concentration.
No adverse effect on the material to be protected, i.e., no discoloration, no deterioration of stability to heat or light, etc.
Compatibility with plasticizers and other additives (stabilizers, slip agents, antioxidants, etc.).
No negative side effects (corrosiveness, skin irritation, or odor of finished product).
Thermal stability and low volatility under processing conditions.
Long shelf life.
Ease of application.
Long-lasting activity in use.
Low toxicity to warm-blooded animals.

These requirements generally are well satisfied by arsenic compounds, and in particular those based on organic arsine derivatives. Preferred are phenoxyarsine compounds, and in particular 10,10'-oxybisphenoxyarsine, or optionally the phenoxyarsine derivatives named in German Pat. No. 16 94 894, which combine a broad spectrum of high antimicrobial activity with lox toxicity to warm-blooded animals. However, it has been found that plastic foil and molded articles incorporating arsenic compounds lose their biocidal activity in actual use in the presence of water after a while and are then again vulnerable to biological attack, as by parasitic growth, for example. Tests run in this connection by storing plastic foils incorporating arsenic compounds in running water have shown that after just 8 to 10 weeks at 20° C. (test conditions) about half of the arsenic content of the foils is lost. In other words, a portion of the arsenic compounds is washed out, as can be demonstrated by measurement of the arsenic content, even though the arsenic compounds used are extremely sparingly soluble in water; and raising the temperature will increase such elution. (See comparative examples.)

Thus there has been a need to assure long-lasting activity of biocidal agents incorporated in plastics by preventing these agents from being washed out while retaining the arsenic compounds based on organic arsine derivatives, which have proved highly effective and have low toxicity to warm-blooded animals.

The invention thus has as its object a biocidal composition based on organic arsenic compounds which is characterized in that it includes tin compounds for the purpose of preventing elution of the arsenic compound.

Surprisingly, the tin compounds used in the biocidal composition effectively prevent the elution of arsenic compounds from plastics by water. In tests conducted in running water, it was found that in the presence of tin compounds the arsenic content of foil and molded articles made from plastics decreases but slightly over a period of up to 8 weeks and then continues to decrease at only a very low rate over periods as long as half a year and even a year.

The specific function of the tin compounds present in the biocidal composition thus is to prevent elution of the arsenic compounds and thus to preserve for an extended period of time the biocidal activity imparted to the plastic through an arsenic compound.

Generally, the amount of the tin compounds must therefore be based on the amount of the arsenic compound. An amount ranging from 0.1 to 5 parts by weight, and preferably from 0.3 to 3 parts by weight, of calculated Sn from the particular tin compound used per part by weight of the arsenic compound should be present in the biocidal composition as well as in the plastic molding compounds and molded articles in which it is incorporated.

A number of tin compounds are widely used as additives for plastics and paints for the purpose of imparting light and heat stability to them. Moreover, a number of tin compounds, and particularly triorganotin compounds, are known for their biocidal activity in the control of parasitic growth on plastics.

However, in the case of the tin compounds in accordance with the present invention, biocidal activity is not a requirement. In fact, tin compounds may advantageously be used which have no biocidal activity or which are nontoxic within the meaning of the pure food laws.

Nor could the known use of tin compounds as additives for plastics have suggested that tin compounds are effective specifically in preventing the elution in accordance with the invention of growth-inhibiting arsenic compounds from plastics.

Suitable tin compounds in accordance with the invention are organotin compounds and tin(II) salts. Suitable organotin compounds are those having moieties R and X bonded to the tin, the moieties R being alkyl radicals having from 1 to 10 carbon atoms, or aryl radicals such as the phenyl radical, and X standing for halogens, sulfur, oxygen, alkoxide groups, moieties of carboxylic acids or carboxylic acid esters as well as thiocarboxylic acids or their esters.

The organotin compounds with the moieties R and X may have one or more and up to about six tin atoms per molecule. Organotin compounds usually are classified into triorgano-, diorgano- and monoorganotin compounds on the basis of the number of organic groups, that is, the alkyl or aryl groups, bonded to each tin atom. Tin compounds of the $R_3SnX$, $R_2SnX_2$ and $RSnX_3$ types have one tin atom per molecule and monovalent moieties R and X. Tin compounds of the $R_2SnX$ type contain a bivalent moiety X, for example, a mercaptocarboxylic acid, and have one tin atom per molecule, while the $(R_3Sn)_2X$ type of tin compound, for example, the bis(trialkyltin) oxides and sulfates, has a bivalent moiety X between two tin atoms. Cyclic structures are found, for example, in dialkyltin sulfides of the formula $(Alk_2Sn-S-)_3$ with two linked alkyl radicals for every tin atom, where three tin atoms linked through bivalent sulfide moieties X form a six-membered ring with the sulfide moieties, and in monoalkylthiostannonic acids of the formula $Alk_4Sn_4S_6$, in which one alkyl radical is bonded to each tin atom, which through three bivalent sulfide moieties X is bonded to three further tin atoms in the manner of an admantane structure.

What organotin compounds have in common thus is tetravalent tin; and in the case of tin compounds which have one tin atom per molecule the number of the always monovalent organic radicals R and the monovalent moieties X is four, or a bivalent moiety X and two organic radicals have four bonds to the tin atom, and in the case of bivalent moieties X as a bridge between two tin atoms there are also four bonds emanating from each tin atom of a ring system. All organotin compounds, regardless of whether they have one or more tin atoms per molecule, thus have at least one organic radical and at least one monovalent or bivalent moiety X per tin atom.

In many di- and monoorganotin compounds having bivalent moieties X, and particularly those of the dicarboxylic acids and mercaptocarboxylic acids described in greater detail further on, substances having one tin atom per molecule and, bonded thereto, a bivalent moiety X are in equilibrium with cyclic compounds containing several tin atoms in which bivalent moieties X form bridges between every two neighboring tin atoms.

In trialkyltin compounds of the $R_3SnX$ and $(R_3Sn)_2X$ types, the propyl and butyl radicals are preferred alkyl radicals. Methyl radicals and the substituted alkyl radical Alk—O—CO—CH—CH$_2$—, wherein Alk has the meaning given above, and preferably methyl, are also being used.

In di- and monoalkyltin compounds, the preferred alkyl radicals are the butyl and octyl radicals. Methyl radicals and said substituted alkyl radical are also in use.

In all of the organotin compounds named, there may be present as monovalent moieties X, from one to three times, halogen groups, and in particular chlorine or fluorine, carboxylic acid moieties and carboxylic acid ester moieties having the structure —(H$_2$C)$_x$—CO—O—Alk, —(CH$_2$)$_x$—O—CO—Alk or —O—CO—Alk, wherein X stands for 1 or 2 and Alk has the meaning given above, and as —O—CO—Alk moiety in particular the acetyl moiety, also long-chain fatty acid moieties having from 10 to 20 carbon atoms, and especially the lauroyl moiety, the alkoxy moiety having from 1 to 10 carbon atoms, and particularly mercaptide and sulfide moieties having the structure —S—(CH$_2$)$_x$—CO—O—Alk, —S—(CH$_2$)$_x$—)—CO—Alk or —S—Alk, wherein X and Alk have the meanings given above. Preferred mercaptide moieties are the butylthioglycol and isooctylthioglycol moieties. Semiesters of saturated or unsaturated dicarboxylic acids, such as maleic acid semiesters, and particularly the methyl ester, are also suitable for use. Bivalent moieties X are oxide, sulfate and sulfide moieties, moieties of saturated and unsaturated dicarboxylic acids, of which fumaric and maleic acid moieties are preferred, and especially thiocarboxylic acid moieties having from 2 to 10 carbon atoms, of which the mercaptoacetyl and 3-mercaptopropionic acid moieties are preferred. Specifically included are bis(tripropyl, tributyl, trioctyl, triisooctyl and trisphenyl)tin oxides and sulfides, the corresponding triorganotin chlorides and fluorides, and the esters of monocarboxylic acids or semiesters of dicarboxylic acids known as tributyl-, trioctyl- and triphenyltin arboxylates, such as acetates, benzoates, pivalates, linolates or malenates; dialkyltin dihalides such as dibutyltin dichloride, di-n-octyltin dichloride amd diphenyltin dichloride; dibutyl- and dioctyltin oxide, dimethyl-, dibutyl- and diphenyltin sulfide as well as dialkyltin dialkoxides in which the mentioned alkyl radicals and alkoxy groups having in particular from 1 to 3 carbon atoms are present; also dibutyl- and dioctyltin dilaurates and diacetates, dibutyl- and dioctyltin dicarboxylic acid semiesters or thiocarboxylic acid semiesters, such as dimaleic acid methyl, butyl or octyl esters, or diorganotin methoxymaleic acid esters, dimethoxymaleic acid methyl esters and diisooctylthioglycolates or maleinates, dimethyltin diisooctylthioglycolate, dibutyltin diisooctylthioglycolate as well as dioctyltin and dibutyltin thioglycol esters, di-n-octyltin S,S'-bis(isooctylmercaptoacetate), and monoorganotin compounds such as n-butyl trichloride, monomethyl- or monobutyltin oxides and sulfides of the adamantane type, as well as monomethyl-, monobutyl- and monooctyltin alkoxides in which one, two or three alkoxy groups, and particularly the ethoxy group, are replaced by dicarboxylic acid semiesters, thiocarboxylic acid semiesters and/or carboxylic acids, such as n-octyltin-tris(isooctyl)thioglycolates or laureate.

Suitable for use as tin(II) salts are, in particular, tin(II) chloride and tin(II) sulfate, optionally in a form containing water of crystallization.

The preferred field of application of the invention is weather-resistant molded articles produced from plastic molding compounds, in particular on the basis of flexible PVC and/or ethylene/vinyl acetate copolymers, or ethylene/vinyl acetate graft polymers with polyvinyl chloride grafted onto them, and optionally polyethylene, which incorporate stabilizers imparting stability to light, weather and heat, and optionally conventional additives such as colorants, fillers and slip agents or the like, in addition to the biocidal composition.

The invention thus has as a further object plastic molding compounds and molded articles produced therefrom which contain the biocidal composition of arsenic compounds and tin compounds.

Contents ranging from 0.005 to 0.08, and preferably from 0.01 to 0.05, parts by weight of an arsenic compound per 100 parts by weight of molding compound will usually suffice for the desired effect, although smaller proportions may be used, if desired.

The tin compounds which will prevent elution of the arsenic compound should be present in amounts ranging from 0.1 to 5.0 parts by weight of calculated tin of a tin compound per part by weight of the arsenic compound.

The weather-resistant products in accordance with the invention which are based on flexible PVC have the advantage of good stability to light, weather and heat, imparted to them through appropriate stabilizers, preferably based on barium-calcium compounds and/or calcium-zinc compounds and/or lead compounds, optionally in combination with further stabilizers, and at the same time remain free of parasitic growth such as algae, microorganisms, etc.

To the extent that the tin compounds used in accordance with the invention are also stabilizers imparting stability to light, weathering, or thermal decomposition during processing or in use, the organotin compounds can, as a side effect, supplement or even replace the basic Ba-Cd, Ca-Zn or lead stabilization. Moreover, the tin compounds preferably selected for use from among those which are suited for use are tin compounds which are substantially harmless toxicologically and have even been approved by the health authorities for use in contact with foods.

The preferred field of application of the invention is products on the basis of flexible PVC which, especially in view of the plasticizers or of the ethylene/vinyl acetate copolymers or graft polymers used, require special stabilization as protection against biological attack.

Applications for products on a flexible PVC basis are, for example, as foils, plates and sealing sheets for the lining or covering of swimming pools, damp rooms, cooling-water tanks, roofs, bridges, tunnels, etc. Molded PVC articles containing the biocidal composition may be used as structural parts or sections exposed to water or outdoor weathering, for example, as parts for tanks, scrubbing towers, clarifying plants, footbridges, pipes, floats, etc. Moreover, the biocidal composition may be added to paints. Suitable plasticizers for molding compounds based on flexible PVC are, in particular, the esters of polybasic acids with monohydric alcohols, such as phthalates, esters of adipic acid and sebacic acid, trimellitates, paraffinsulfonic acid and phenyl/cresyl esters, from 15 to 50 parts by weight of plasticizer being preferably used per 100 parts by weight of PVC molding compound.

Polyvinyl chloride can be plasticized not only by the addition of low-molecular-weight plasticizers but may also contain plasticizing high-polymer additives such as ethylene/vinyl acetate, or ethylene/vinyl acetate copolymers or graft polymers, chlorinated polyethylene or the like, or may be formed in whole or in part of the copolymers or graft polymers. The molding compounds in accordance with the invention may contain from 20 to 80 parts by weight of plasticizing high-polymer additives per 100 parts by weight of molding compound; however, plasticizer and high-polymer additive together should not amount to more than 80 weight percent of the molding compound. Because of their content of grafted PVC, EVA graft polymers may constitute the entire synthetic-resin component of the molding compound.

It has been found that the use of the biocidal composition in accordance with the invention produces very good results which cannot be obtained by the use of the arsenic compound alone or of the tin compound alone.

Arsenic compounds are highly effective against biological attack, and many organic arsenic compounds do not have the toxicity to warm-blooded animals that is typical of other arsenic compounds. The drawback which has afflicted precisely these organic arsenic compounds, namely, their elutability from plastics, is now being overcome, or reduced to the extent desirable for a given application, through the tin component of the biocidal composition.

The effectiveness of biocidal agents is generally tested by a procedure borrowed from bacteriology, namely, by inoculating the surface of the specimen with suspended microorganisms and then "incubating" it. The colonies of microorganisms which appear around inoculated spots on specimens lacking a biocidal component are either reduced in number and size or are absent altogether when active biocidal agents are present in the surface.

Frequently the effectiveness of a biocidal substance is evaluated on the basis of the zone of inhibition (sterile zone) forming around the sample. The larger this zone is, the higher the biocidal activity of the substance is assumed to be.

This approach is well suited to short-lived products. In the case of long-lived products, the high elution in accordance with the prior art and the reduced elutability in accordance with the invention must be taken into consideration.

The examples which follow point up in particular the effectiveness of the tin compounds of Examples 2 to 13 by comparison with Example 1. In the Examples 2 et seq. in accordance with the invention, the arsenic content of the foil is not reduced at all, or then only slightly, over the first 6 to 8 weeks of exposure to running water, and elution is hardly greater at 30° C. than at 20° C. On the other hand, the arsenic content of a foil to which no tin compounds have been added (Example 1) is reduced after just 6 to 8 weeks at 20° C. to one-half, and at 30° C. to about one-third.

From the long-term test of Table 2 it is apparent that while the arsenic content drops over an extended testing period ranging from 10 to 52 weeks, it then stays at a practically constant level, so that the desired long-term biocidal activity is preserved.

It will be appreciated that the instant specification and examples are set forth by way of illustration and not of limitation, and that various changes and modifications may be made without departing from the spirit and scope of the present invention.

EXAMPLES

The basic formulation used in Examples 1 to 8 consisted of 60 parts by weight flexible PVC, 40 parts by weight of a $C_8$-to-$C_{10}$ alkyl phthalate plasticizer, 3.8 parts by weight of a predominantly lead-based PVC stabilizer, and 1.5 parts by weight of conventional paint pigments.

The material samples used in testing and evaluation were produced by calendering in a thickness of 1.2 mm.

EXAMPLE 1 (COMPARISON)

To a basic formulation of the composition described above there was added 0.05 part by weight 10,10'-oxybisphenoxy-arsine, and from this mixture a foil 1.2 mm thick was produced by calendering. A foil sample measuring 35 cm² was then suspended in a vessel containing water of a temperature of 20° C. and 30° C., respectively. (Water replaced once in about 1.5 hours through continuous inflow and outflow.) The As content was then determined after different exposure times. The results of the tests are presented in Table 1.

TABLE 1

| Immersion time | Example |   |   |   |   |   |   |   |
|---|---|---|---|---|---|---|---|---|
|  | 1 | 2 | 3 | 4 | 5 | 6 | 7 | 8 |
| 10,10'-Oxybisphenoxyarsine content in fresh material, in parts by weight | | | | | | | | |
|  | 0.050 | 0.050 | 0.050 | 0.050 | 0.050 | 0.050 | 0.050 | 0.050 |
| 10,10'-Oxybisphenoxyarsine content in sample material after immersion in running water at 20° C. in parts by weight | | | | | | | | |
| 1 week | 0.0486 | 0.048 | 0.048 | 0.045 | 0.048 | 0.0486 | 0.0486 | 0.0486 |
| 2 weeks | 0.0417 | 0.048 | 0.048 | 0.045 | 0.041 | 0.0486 | 0.0486 | 0.0417 |
| 4 weeks | 0.0347 | 0.048 | 0.048 | 0.045 | 0.041 | 0.0486 | 0.0486 | 0.0382 |
| 8 weeks | 0.0243 | 0.045 | 0.048 | 0.041 | 0.038 | 0.0486 | 0.0486 | 0.0347 |

TABLE 1-continued

| Immersion time | Example | | | | | | | |
|---|---|---|---|---|---|---|---|---|
| | 1 | 2 | 3 | 4 | 5 | 6 | 7 | 8 |
| 10,10'-Oxybisphenoxyarsine content in sample material after immersion in running water at 30° C., in parts by weight | | | | | | | | |
| 1 week | 0.0417 | 0.0486 | 0.0486 | 0.0452 | 0.0452 | 0.0452 | 0.0452 | 0.0452 |
| 2 weeks | 0.0313 | 0.0452 | 0.0417 | 0.0452 | 0.0382 | 0.0452 | 0.0452 | 0.0382 |
| 4 weeks | 0.0313 | 0.0452 | 0.0382 | 0.0382 | 0.0382 | 0.0417 | 0.0417 | 0.0347 |
| 8 weeks | 0.0173 | 0.0417 | 0.0382 | 0.0347 | 0.0382 | 0.0417 | 0.0417 | 0.0313 |

EXAMPLES 2 TO 8

Example 1 was repeated, except that the following amounts of tin compounds were added to the formulation:

| Example 2 | 0.6 part by weight trialkyltin compound corresponding to 0.158 part by weight Sn | [1] |
| Example 3 | 1.0 part by weight dibutyltin mercaptide compound corresponding to 0.159 part by weight Sn | [2] |
| Example 4 | 1.1 parts by weight dibutyltin carboxylate compound corresponding to 0.153 part by weight Sn | [3] |
| Example 5 | 0.85 part by weight dibutyltin maleic acid ester corresponding to 0.162 part by weight Sn | [4] |
| Example 6 | 0.95 part by weight ester-tin compound corresponding to 0.157 part by weight Sn | [5] |
| Example 7 | 0.85 part by weight dimethyltin compound corresponding to 0.157 part by weight Sn | [6] |
| Example 8 | 0.25 part by weight tin(II) chloride corresponding to 0.157 part by weight Sn | |

[1] Irgarol 541 L (Ciba-Geigy)
[2] Irgastab 17 M (Ciba-Geigy)
[3] Irgastab T 150 (Ciba-Geigy)
[4] Irgastab T 4 (Ciba-Geigy)
[5] Irgastab T 649 (Ciba-Geigy)
[6] Irgastab T 31 P (Ciba-Geigy)

The arsenic contents of the foil after elution by running water in accordance with Example 1 are presented in Table 1.

While the tin-free comparison sample from Example 1 showed a definite arsenic loss due to elution by water, all tin-containing foils (Examples 2 to 8) exhibited substantially lower arsenic losses. This was true also in the case of the tin(II) chloride, which is readily soluble in water.

EXAMPLE 9

Using the basic formulation, a foil was produced with 0.025 part by weight 10,10'-oxybisphenoxyarsine and 0.3 part by weight of a trialkyltin compound (Irgarol BI 541 L of Ciga-Geigy; Sn content, 0.079 part by weight) and then eluted with water as described in Example 1.

The arsenic contents of the foil after elution with running water are compared in Table 2 with the values from Examples 1 and 2.

EXAMPLES 10 TO 13

In these examples, 0.050 part by weight 10,10'-oxybisphenoxyarsine was added to the basic formulation along with different amounts of the trialkyl tin compound of Example 9 in order to demonstrate the influence of the tin content on the elutability of the arsenic.

The following amounts of the trialkyltin compound were added to the basic formulation according to Example 1:

| Example | Parts by weight Sn | Weight ratio As compound to Sn |
|---|---|---|
| 1 | 0.000 | — |
| 2 | 0.158 | 1:3.16 |
| 10 | 0.118 | 1:2.36 |
| 11 | 0.079 | 1:1.58 |
| 12 | 0.026 | 1:0.52 |
| 13 | 0.016 | 1:0.32 |

The arsenic contents of the foil after elution with running water are presented in Table 3 for comparison.

TABLE 2

| Example | 1 | | 2 | | 9 | |
|---|---|---|---|---|---|---|
| In fresh material | | | | | | |
| 10,10'-Oxybisphenoxy-arsine, parts by weight | 0.050 | (=100%) | 0.050 | (=100%) | 0.025 | (=100%) |
| Sn, parts by weight | — | | 0.158 | | 0.079 | |
| 10,10'-Oxybisphenoxyarsine content of sample material after immersion in running water at 20° C., in parts by weight | | | | | | |
| Immersion | | | | | | |
| 1 week | 0.0486 | 97.2% | 0.0486 | 97.2% | 0.0243 | 97.2% |
| 4 weeks | 0.0347 | 69.4% | 0.0486 | 97% | 0.0243 | 97.2% |
| 8 weeks | 0.0243 | 48.6% | 0.0452 | 90.4% | 0.0208 | 83.2% |
| 20 weeks | 0.0173 | 34.6% | 0.0382 | 76.4% | 0.0208 | 83.2% |
| 36 weeks | 0.0140 | 28.0% | 0.0382 | 76.4% | 0.0713 | 69.2% |
| 52 weeks | 0.0140 | 28.0% | 0.0382 | 76.4% | 0.0173 | 69.2% |
| 10,10'-Oxybisphenoxyarsine content of sample material afer immersion in running water at 30° C., in parts by weight | | | | | | |
| Immersion | | | | | | |
| 1 week | 0.0417 | 83.4% | 0.0486 | 97.2% | 0.0243 | 97.2% |
| 4 weeks | 0.0313 | 62.6% | 0.0452 | 90.4% | 0.0243 | 97.2% |
| 8 weeks | 0.0173 | 34.6% | 0.0417 | 83.4% | 0.0208 | 83.2% |
| 20 weeks | 0.0140 | 28.0% | 0.0347 | 69.4% | 0.0173 | 69.2% |
| 36 weeks | 0.0104 | 20.8% | 0.0347 | 69.4% | 0.0173 | 69.2% |
| 52 weeks | 0.0104 | 20.8% | 0.0347 | 69.4% | 0.0140 | 56.0% |

TABLE 3

| Example | 1 | 2 | 10 | 11 | 12 | 13 |
|---|---|---|---|---|---|---|
| Fresh material | | | | | | |
| 10,10′-Oxy-bisphenoxyarsine, parts by weight | 0.050 | 0.050 | 0.050 | 0.050 | 0.050 | 0.050 |
| Sn, parts by weight | 0.0 | 0.158 | 0.118 | 0.079 | 0.026 | 0.016 |
| 10,10′-Oxybisphenoxyarsine content of sample material after immersion in running water at 20° C., in parts by weight | | | | | | |
| Immersion time | | | | | | |
| 1 week | 0.0486 | 0.0486 | 0.0486 | 0.0486 | 0.0486 | 0.0486 |
| 2 weeks | 0.0417 | 0.0486 | 0.0486 | 0.0486 | 0.0486 | 0.0486 |
| 4 weeks | 0.0347 | 0.0486 | 0.0486 | 0.0486 | 0.0452 | 0.0452 |
| 8 weeks | 0.0243 | 0.0452 | 0.0486 | 0.0486 | 0.0452 | 0.0452 |
| 10,10′-Oxybisphenoxyarsine content of sample material after immersion in running water at 30° C., in parts by weight | | | | | | |
| Immersion time | | | | | | |
| 1 week | 0.0417 | 0.0486 | 0.0486 | 0.0486 | 0.0452 | 0.0452 |
| 2 weeks | 0.0313 | 0.0452 | 0.0452 | 0.0452 | 0.0452 | 0.0417 |
| 4 weeks | 0.0313 | 0.0452 | 0.0452 | 0.0417 | 0.0382 | 0.0382 |
| 8 weeks | 0.0173 | 0.0417 | 0.0417 | 0.0417 | 0.0382 | 0.0382 |

It is apparent from this table that with respect to their elution-inhibiting effect tin compounds are effective over a wide range of arsenic concentrations.

EXAMPLE 14

Example 3 was repeated with the arsenic- and tin-compound contents there specified; however, the following basic formulation was used:
- 58 parts by weight suspension PVC (K value, 70)
- 40 parts by weight EVA (VA component, 45 wt. %)
- 2 parts by weight epoxidized soybean oil
- 2 parts by weight Ba-Cd stabilizer
- 0.7 part by weight slip agent The results of elution tests run were consistent with those of Example 3.

EXAMPLE 15

Example 3 was repeated with the arsenic- and tin-compound contents there specified; however, the following basic formulation was used:
- 92 parts by weight graft polymer PVC on EVA (31.5 et. % VA in the graft polymer; basis EVA with 63 wt. % VA)
- 8 parts by weight dioctyl phthalate plasticiser
- 2 parts by weight Ba-Cd stabilizer
- 0.8 part by weight slip agent The results of elution tests run were consistent with those of Example 3.

The commercial tin compounds used in the examples contain the following tin compounds:

Irgarol 541 L
 50% tributyltin tetrachlorophthalate
 50% tributyltin oleate
Irgastab 17 M—Dibutyltin bisthioglycolic acid ester
Irgastab T 150—Dibutyltin bismaleic acid isobutyl semiester
Irgastab T 4—Dibutyltin bismaleic acid isobutyl semiester
Irgastab T 649—Di-2-carbobutoxyethyltin bisthioglycol isooctyl ester
Irgastab T 31 M—Dimethyltin bisthioglycolic acid ester It will be understood that the specification and examples are illustrative but not limitative of the present invention and that other embodiments within the spirit and scope of the invention will suggest themselves to those skilled in the art.

What is claimed is:

1. A biocidal composition comprising a plastic molding composition of flexible polyvinylchloride, polyethylene, or ethylene/vinylacetate copolymers, containing at least 10,10′-oxy-bis-phenoxyarsine and at least one organo-tin compound of the formula $RSnX_3$, $R_2Sn(X)_m$, $(R_3Sn)_mX$, $Alk_4Sn_4S_6$, or an Sn II salt in an amount of 0.1 to 5.0 parts by weight based on the tin content in said compound or salt per part by weight of the arsenic compound, to prevent elution of the arsenic compound from said composition wherein R is an alkyl radical having from 1 to 10 carbon atoms, or an aryl radical, X is a halogen, sulfur, oxygen, an alkoxide group or carboxylic acid moiety, carboxylic acid ester, thiocarboxylic acid moiety or an ester thereof, Alk is alkyl of 1 to 10 carbon atoms and m=1 or 2.

2. The biocidal composition of claim 1 containing, as a stabilizer, at least one of barium-cadmium compounds, lead compounds and calcium-zinc compounds.

3. The biocidal composition of claim 1 having a content of from 15 to 50 parts by weight of a plasticizer.

4. The biocidal composition of claim 3, wherein said plasticizer is an ester of a polybasic acid with a monohydric alcohol.

5. The biocidal composition of claim 3, wherein said plasticizer is at least one member of the group consisting of phthalates, esters of adipic acid and sebacic acid, trimellitic acid esters, paraffinsulfonic acid phenyl/cresyl ester, aliphatic and aromatic phosphoric acid esters and chloroparaffins, based on 100 parts by weight of the composition.

6. The biocidal composition of claim 1 containing from 20 to 80 parts by weight of plasticizing polymeric additives selected from ethylene/vinyl acetate copolymers and chlorinated polyethylenes, based on 100 parts by weight of the biocidal composition.

7. The biocidal composition of claim 6, wherein the plasticizer and high-polymer additive together do not amount to more than 80 parts by weight of the biocidal composition.

8. A molded article produced from the biocidal composition of claim 1.

9. The molded article of claim 8 in the form of a flat foil, plate, sheet, or surface coating.

10. A method of preventing elution of 10,10′-oxy-bis-phenoxyarsine used in a plastic molding composition of flexible, polyvinylchloride, polyethylene, or ethylene/-vinylacetate copolymers, which method comprises adding to said composition an organo-tin compound of the formula $RSnX_3$, $R_2Sn(X)_m$, $(R_3Sn)_mX$, $Alk_4Sn_4S_6$, or an Sn II salt in amounts of 0.1 to 5.0 parts by weight based on the tin content in said compound or salt per part by weight of the arsenic compound, to substantially prevent or inhibit elution of said arsenic compound from said plastic molding composition wherein R is an alkyl radical having from 1 to 10 carbon atoms, or an aryl radical, X is a halogen, sulfur, oxygen, an alkoxide group or carboxylic acid moiety, carboxylic acid ester, thiocarboxylic acid moiety or an ester thereof, Alk is alkyl of 1 to 10 carbon atoms and m=1 or 2.

11. A method as claimed in claim 10, wherein said plastic molding composition is based on flexible polyvinylchloride.

12. The method of claim 10 wherein said organo-tin compound is selected from the group consisting of tributyltin oleate, tributyltin tetrachlorophthalate, dibutyltin bis maleic acid octyl half ester, dibutyltin bis maleic acid isobutyl half ester and the Sn II salt is tin dichloride.

13. The method of claim 10 wherein said organotin compound is selected from the group consisting of a dibutyl tin mercaptide, a dibutyl tin bis thioglycolic acid octyl to decyl ester, a di-2-carbobutoxyethyltin and a dimethyl tin bis thioglycolic hexyl to octyl acid ester.

14. The composition of claim 1 wherein said at least one organotin compound is selected from the group consisting of tributyltin oleate, tributyltin tetrachlorophthalate, dibutyltin bis maleic acid octyl half ester and dibutyltin bis maleic acid isobutyl half ester.

15. The composition of claim 1 wherein said at least one organotin compound is selected from the group consisting of a dibutyltin mercaptide, a dibutyltin bis thioglycolic acid octyl to decyl ester, a di-2-carbobutoxyethyltin and a dimethyltin bis thioglycolic hexyl to octyl acid ester.

* * * * *

UNITED STATES PATENT AND TRADEMARK OFFICE
CERTIFICATE OF CORRECTION

PATENT NO. : 4,666,956

DATED : May -19,1987

INVENTOR(S) : Paul Spielau et al

It is certified that error appears in the above-identified patent and that said Letters Patent is hereby corrected as shown below:

Column 3, line 2 "admantane" should read --adamantane--.

Column 8, line 58, Table 2 entry under 36 weeks  "0.0713" should read --0.0173--.

Signed and Sealed this

Eighteenth Day of September, 1990

Attest:

HARRY F. MANBECK, JR.

Attesting Officer

Commissioner of Patents and Trademarks